US009949365B2

(12) United States Patent
Wynn (10) Patent No.: US 9,949,365 B2
(45) Date of Patent: Apr. 17, 2018

(54) AIR COOLED INLINE SENSOR LIGHT SOURCE WITH SOLID STATE UV EMITTER

(71) Applicant: Endress+Hauser Conducta Inc., Anaheim, CA (US)

(72) Inventor: William H. Wynn, Hillsborough, CA (US)

(73) Assignee: Endress+Hauser Conducta Inc., Anaheim, CA (US)

( * ) Notice: Subject to any disclaimer, the term of this patent is extended or adjusted under 35 U.S.C. 154(b) by 230 days.

(21) Appl. No.: 14/630,134

(22) Filed: Feb. 24, 2015

(65) Prior Publication Data

US 2015/0237719 A1  Aug. 20, 2015

Related U.S. Application Data

(63) Continuation-in-part of application No. 12/881,438, filed on Sep. 14, 2010.

(51) Int. Cl.

| G01J 1/42 | (2006.01) |
| H05K 1/02 | (2006.01) |
| G01N 21/33 | (2006.01) |
| H05K 1/18 | (2006.01) |
| H05K 7/20 | (2006.01) |

(52) U.S. Cl.
CPC ........... H05K 1/0274 (2013.01); G01N 21/33 (2013.01); H05K 1/0203 (2013.01); H05K 1/18 (2013.01); H05K 7/20127 (2013.01); H05K 2201/10106 (2013.01)

(58) Field of Classification Search
CPC ..... H01L 33/648; H01L 33/64; F21V 29/004; F21V 29/002; F21V 29/20; F21V 29/503; F21V 29/30
See application file for complete search history.

(56) References Cited

U.S. PATENT DOCUMENTS

| 5,479,320 A | 12/1995 | Estes et al. |
| 6,403,966 B1 | 6/2002 | Oka |
| 7,214,952 B2 | 5/2007 | Klipstein et al. |
| 2003/0080193 A1 | 5/2003 | Ryan et al. |

(Continued)

FOREIGN PATENT DOCUMENTS

| DE | 102005028113 B4 | 8/2007 |
| JP | 2002005826 A | 1/2002 |

OTHER PUBLICATIONS

Hanrahan, Grady, et al., "HighTemporal and Spatial Resolution Environmental Monitoring using Flow Injection with Spectroscopic Detection", Trends in Analytical Chemistry, vol. 21, No. 4, pp. 233-239 (2002).

*Primary Examiner* — Kenneth J Malkowski
(74) *Attorney, Agent, or Firm* — Edward S. Wright (57) ABSTRACT

Light source for an inline sensor having one or more solid state UV emitters for emitting light at single wavelengths in the range of 240 to 400 nm. The light emitted by each of the emitters has a bandwidth on the order of 10-20 nm and is directed toward a measurement detector in the inline sensor. The UV emitters are enclosed in a housing which can be attached to the inline sensor, with a reference detector and a regulator for the UV emitters also within the housing, and an aperture through which the light passes from the emitters to the measurement detector. In some embodiments, air cooling is provided for the UV emitters.

16 Claims, 8 Drawing Sheets

(56) References Cited

U.S. PATENT DOCUMENTS

| | | |
|---|---|---|
| 2005/0133724 A1 | 6/2005 | Hsich et al. |
| 2006/0284101 A1 | 12/2006 | Peskov et al. |
| 2007/0120343 A1* | 5/2007 | Spence ................ B60Q 1/2661 280/291 |
| 2007/0121326 A1* | 5/2007 | Nall ...................... F21V 29/004 362/294 |
| 2008/0220535 A1 | 9/2008 | LeBoeuf et al. |
| 2009/0068856 A1 | 3/2009 | Low |
| 2012/0001991 A1* | 1/2012 | Onozawa ............... B41J 2/1714 347/102 |

* cited by examiner

AIR COOLED INLINE SENSOR LIGHT SOURCE WITH SOLID STATE UV EMITTER

RELATED APPLICATION

Continuation-in-Part of Ser. No. 12/881,438, filed Sep. 14, 2010.

BACKGROUND OF THE INVENTION

Field of Invention

This invention pertains generally to inline sensors and measurements and, more particularly, to an air cooled ultraviolet (UV) light source for use in such applications.

Related Art

Inline UV sensors are widely used in industrial and pharmaceutical applications. Heretofore, low and medium pressure gas discharge lamps have been used as the light source in making such measurements. In pharmaceutical applications, the light source most commonly used is a low pressure mercury (Hg) lamp which emits discrete lines of light at a plurality of specific wavelengths in the UV and visible spectrum. To isolate specific emission lines or wavelengths of interest, bandpass interference filter must be used. Such filters greatly reduce the available optical signal, particularly in the UV spectrum where the transmission of the filters rarely exceeds 20 percent.

The low pressure Hg lamp assemblies commonly used for inline sensor applications typically require approximately 4-5 watts of power, and the overall efficiency is low and distributed across the many discrete spectral lines emitted by the lamp. These lamps exhibit optical noise and tend to drift in output, dissipate heat due to operation at high envelope temperatures, and require special high voltage power supplies.

To compensate for variations in lamp output and maintain accurate results, measurement signals and reference signals are monitored and compared. To isolate a spectral line of interest, matched filters must be used for both the reference signals and the measurement signals. In dual beam applications, the optical requirements are further complicated since matched filters and detectors are required for each reference and measurement channel, and the channels must be isolated. This can be done, for example, either by the use of a side-by-side filter/detector configuration or by the use of beam splitting, either of which will result in a further reduction of the optical signals.

If the desired wavelength is not one of the available emission lines, the lamp is coated with a phosphor which fluoresces at the desired wavelength when excited by one of the available lines, and efficiency is further reduced.

Figure 1:
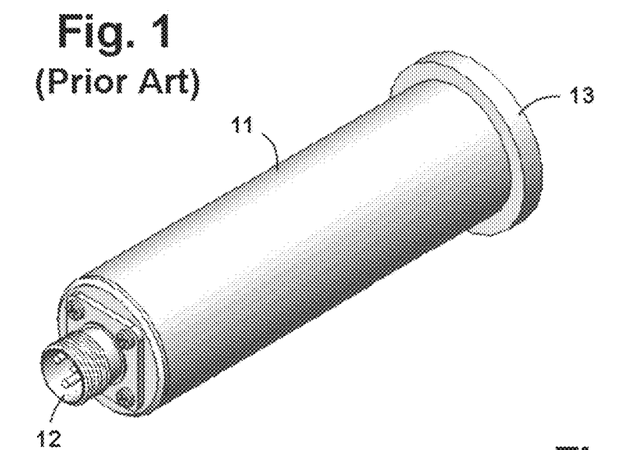
FIG. 1 is an isometric view of a UV light source of the prior art.
Figure 2:
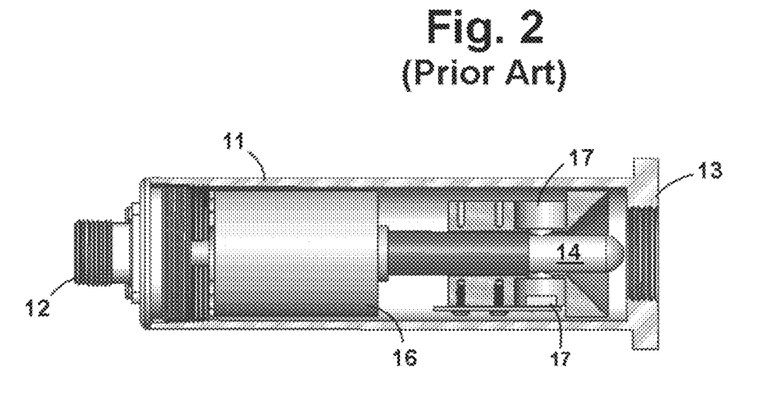
FIG. 2 is a vertical sectional view of the prior art light source of FIG. 1.

A typical low pressure Hg lamp assembly of the prior art is illustrated in FIGS. 1-2. This assembly has a cylindrical housing 11 with an electrical connector 12 at one end and a fitting 13 at the other end for connection to a flow cell. A low pressure Hg lamp 14 and a high voltage power supply 16 are enclosed within the housing along with reference detectors and filters 17, 17. As these drawings illustrate, due to the relatively large sizes of the lamp and its power supply, the overall assembly is also relatively large in size and cumbersome to use.

Figure 3:
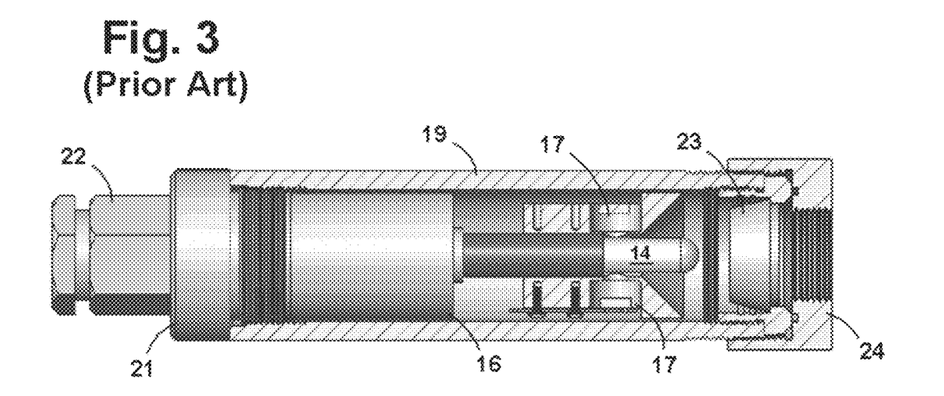
FIG. 3 is a vertical sectional view of another UV light source of the prior art.

Another problem with low pressure Hg lamps is that when they are used in hazardous environments, special containment enclosures and connectors must be employed to meet safety requirements. These requirements typically include an approved housing that is capable of containing explosions in the event the gas in the lamp should ignite and special cabling which will isolate electrical signals from the hazardous environments. As illustrated in FIG. 3, such a device typically includes an explosion proof housing 19 with an explosion proof end cap 21 and an explosion proof cable gland 22 at one end and an explosion proof window assembly 23 and a flow cell adapter 24 at the other end.

OBJECTS AND SUMMARY OF THE INVENTION

It is, in general, an object of the invention to provide a new and improved UV light source for use in inline sensor applications.

Another object of the invention is to provide a UV light source of the above character which is air cooled.

These and other objects are achieved in accordance with the invention by providing a light source for an inline sensor having one or more solid state UV emitters for emitting light at single wavelengths in the range of 240 to 400 nm. The light emitted by each of the emitters has a bandwidth on the order of 10-20 nm and is directed toward a measurement detector in the inline sensor. The UV emitters are enclosed in a housing which can be attached to the inline sensor, with a reference detector and a regulator for the UV emitters also within the housing, and an aperture through which the light passes from the emitters to the measurement detector. The UV sensors are cooled by air which flows through the housing and is directed toward the sensors.

DETAILED DESCRIPTION

Figure 4:
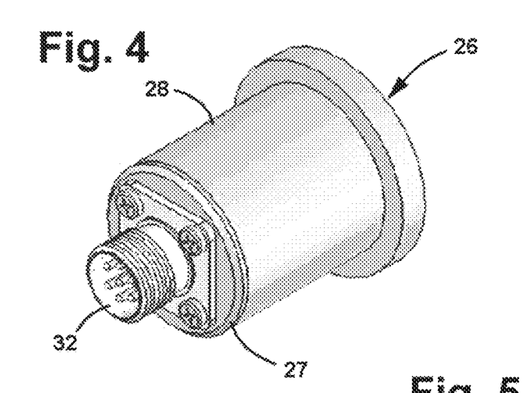
FIG. 4 is an isometric view of one embodiment of a UV light source incorporating the invention.
Figure 5:
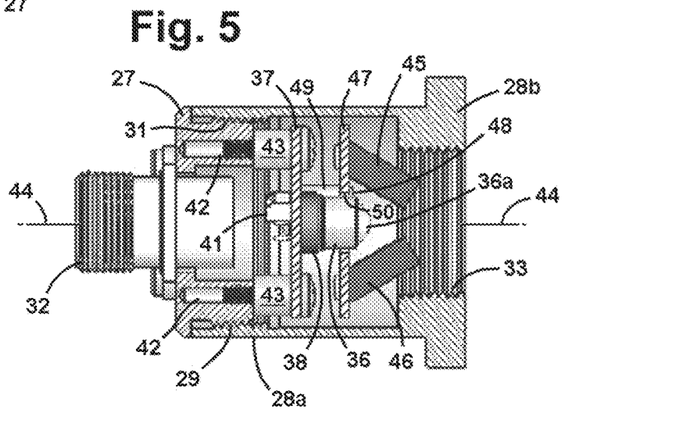
FIG. 5 is a vertical sectional view of the embodiment of FIG. 4.

As illustrated in FIGS. 4 and 5, the light source has a housing 26 with a generally circular base 27 and a removable cover 28 consisting of a cylindrical side wall 28a and an end wall 28b formed integrally with the side wall. The base has external threads 29 which mate with internal threads 31 on the side wall to secure the cover and base together. An electrical connector 32 is mounted on the outer side of the base for connection to external circuits which carry electrical signals and power for the device, and end wall 28b has a threaded aperture 33 for connection to an inline sensor.

A solid state UV emitter or LED (light emitting diode) 36 is mounted on a circuit board 37 within the housing. Unlike the low pressure Hg lamps used with other inline sensors, these emitters deliver emissions at a single wavelength with a bandwidth on the order of 10-20 nm. The emissions are spectrally pure, with a power on the order of 0.5-1.5 milliwatts which is concentrated at the desired wavelength. Such emitters are currently available at 10-20 nm intervals within a spectral range of about 240 to 400 nm.

The emitter is mounted in a socket 38 on circuit board 37 along with circuitry 41 for regulating the current and, hence, the power supplied to the emitter. The circuit board is mounted to the base 27 of the housing by mounting screws 42 and spacers 43, with the emitter being disposed coaxially within the housing and facing toward the aperture 33 in end wall 28b.

The emitter has a lens 36a which focuses the emissions along the axis 44 of housing 26 and aperture 33. With the lens incorporated in the emitter, there is no need for other mirrors, reflectors and/or lenses for focusing and/or directing the emissions. Moreover, with the emissions being produced only at the wavelength and bandwidth desired, optical filtering is not required in either the light source or the sensor.

A pair of reference detectors 45, 46 are mounted on a second circuit board 47 which is mounted to the regulator board 37 by mounting screws 48 and spacers 49, with emitter 36 extending through a central opening 50 in the second board. Spacers 49 are electrically conductive and provide electrical connections between the two boards as well as aligning the boards with each other. The detectors face the aperture and are inclined at an angle on the order of 30 degrees to the axis of emission.

With this source, replacement or changing of the emitter is easy to do and, if desired, can be done without disconnecting the source from the inline sensor. To do so, base 27 is unscrewed from the cover 28 of the housing, and the base and circuit boards are withdrawn as a unit from the housing. Detector board 47 is then removed from regulator board 37, following which the emitter can be removed from its socket and replaced.

Since no filters are required either for the reference detectors or for the measurement detectors, the operational wavelength of the source and, hence, the sensor can be changed simply by changing the solid state UV emitter to one of the desired wavelength.

The power requirement of the solid state UV emitter is only about 50-100 milliwatts, which is low enough for safe operation in explosive environments. Since the power is low, such emitters are classified as intrinsically safe devices which can be operated in hazardous environments using intrinsic safety barriers. This means that the light source can be operated in most hazardous environments without explosion proof containers and/or special wiring.

Figure 6:
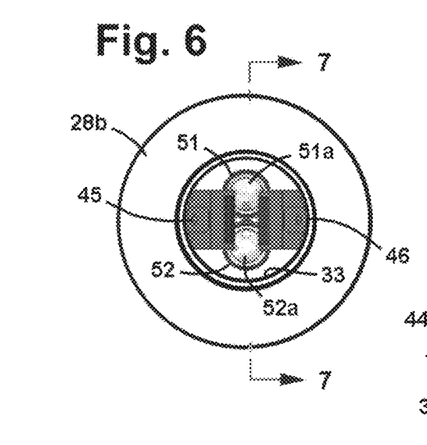
FIG. 6 is a front elevational view of another embodiment of a UV light source incorporating the invention.
Figure 7:
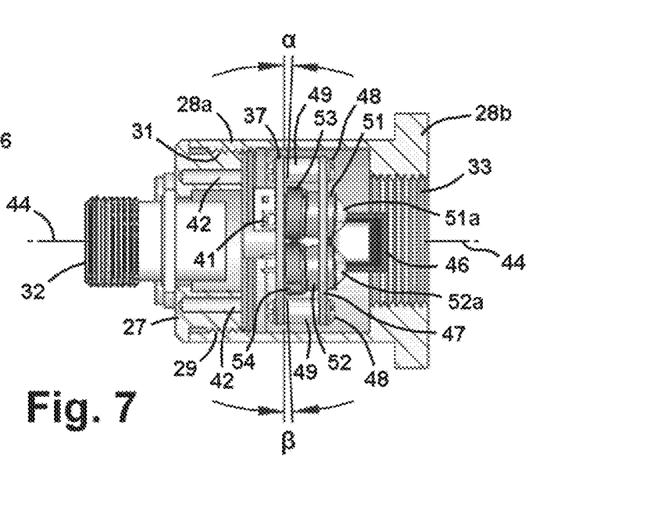
FIG. 7 is a cross-sectional view taken along line 7-7 in FIG. 6.

FIGS. 6 and 7 illustrate a dual beam embodiment of the light source which is similar to the single beam embodiment of FIGS. 4 and 5, with like reference numerals designating corresponding elements in the two embodiments. In the dual beam source, a pair of solid state UV emitters 51, 52 are mounted side-by-side on circuit board 37, and the voltage regulator circuitry 41 on the board has the capacity to provide operating power to the two emitters. The emitters are mounted in sockets 53, 54, and the emissions from the two emitters are focused on the measurement detector by adjusting the angles between the sockets and the board. In the embodiment illustrated, the angles $\alpha$ and $\beta$ between the sockets and the board and, hence the angles between the beams and axis 44 are on the order of 2.5 degrees.

Each of the emitters 51, 52 is similar to emitter 36, and can be of any desired operational wavelength. In the embodiment illustrated, the two emitters operate at wavelengths of 280 nm and 254 nm, respectively.

Figure 8:
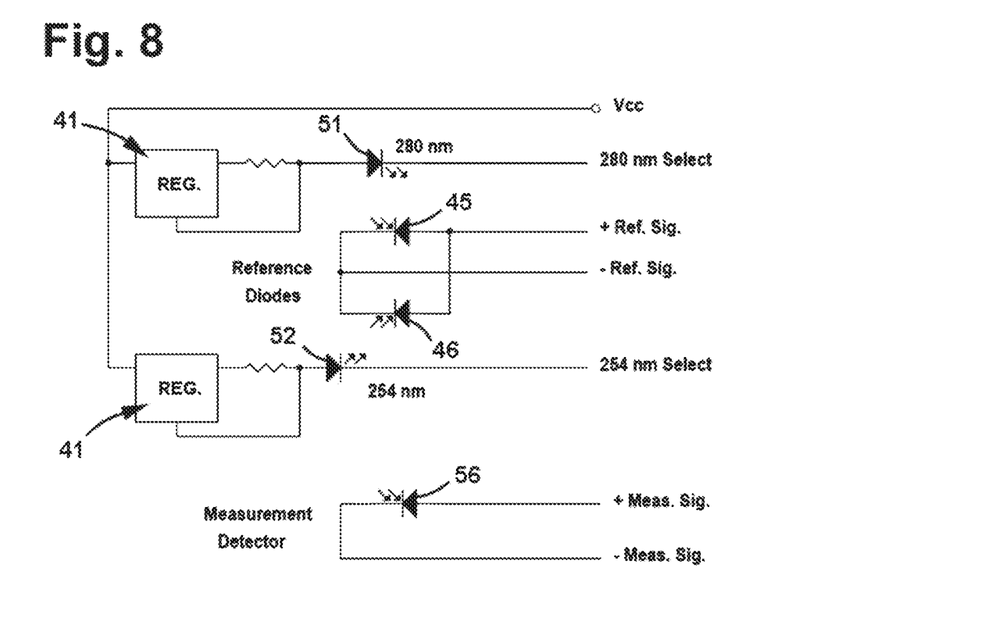
FIG. 8 is a simplified circuit diagram of the embodiment of FIG. 6.

As illustrated in FIG. 8, the supply voltage Vcc is applied to the regulator circuits, the outputs of the regulators are connected to the anodes of emitters 51, 52, and SELECT signals are applied to the cathodes of the emitters. Reference diodes 45, 46 are connected electrically in parallel and provide reference signals +Ref.Sig. and −Ref.Sig., and the measurement detector 56 in the inline sensor provides measurement signals +Meas.Sig. and −Meas.Sig. corresponding to the emissions impinging thereon.

The voltage Vcc is current regulated to each of the UV emitting diodes, and the regulators can be individually adjusted to match their respective outputs to the measurement detector. In the embodiment illustrated, the sensor has only one measurement diode which detects the emissions from both of the UV emitters.

Figure 9:
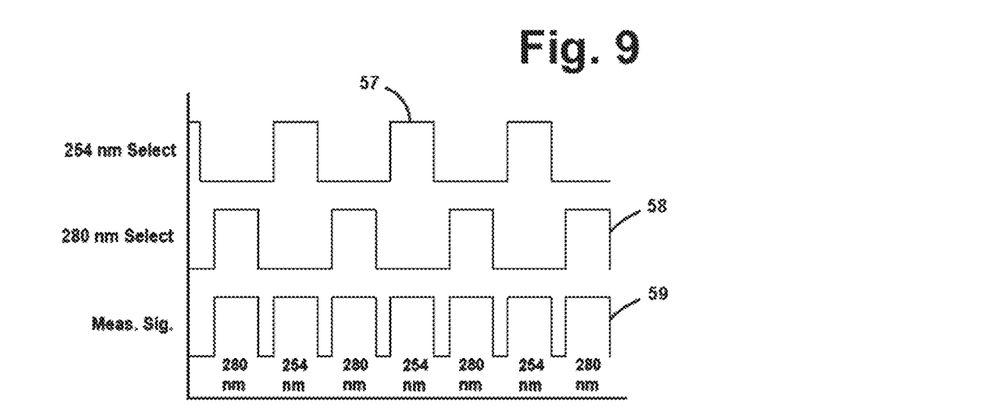
FIG. 9 is a timing diagram illustrating the operation of the embodiment of FIG. 6.

As illustrated in the timing diagram of FIG. 9, UV emitters 51, 52 are turned on alternately by selection signals 57, 58, and measurement detector 56 responds to whichever emitter is active, producing an output signal 59 which alternates between 280 nm and 254 nm in synchronization with the activation of the emitters. This signal can be processed by a single amplifier for further processing and display.

Solid state UV emitters are commonly packaged in standard TO-39 packages, and additional channels can be provided simply by adding additional emitters to the regulator circuit board and driving them in sequence.

In the embodiment of FIGS. 10-15, the light source 61 is illustrated in conjunction with a flowcell 62 and a detector 63 which can, for example, be of the type illustrated and described in copending application Ser. No. 13/398,084, filed Feb. 6, 2012, now U.S. Pat. No. 9,279,746, the disclosure of which is incorporated herein by reference.

Figure 10:
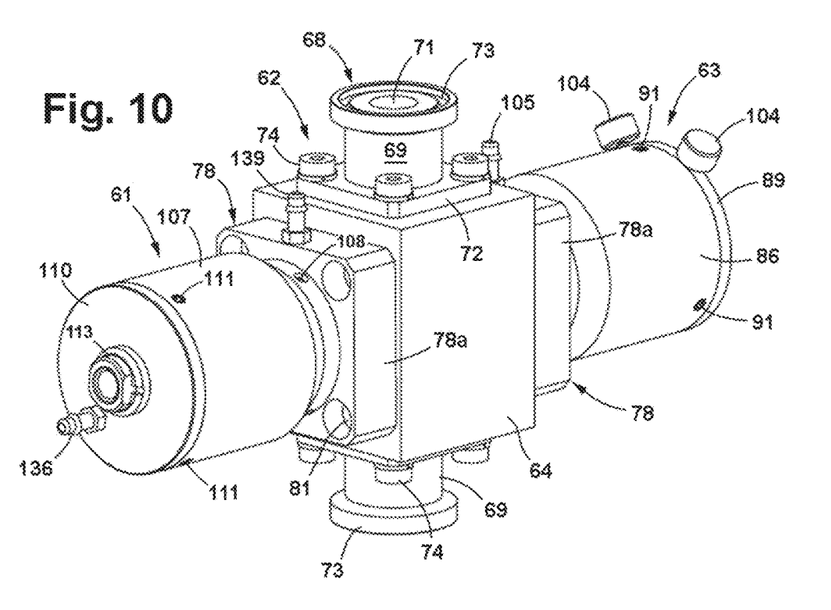
FIG. 10 is an isometric view of an embodiment of an optical sensor with a modular flowcell and a UV light source according to the invention.
Figure 11:
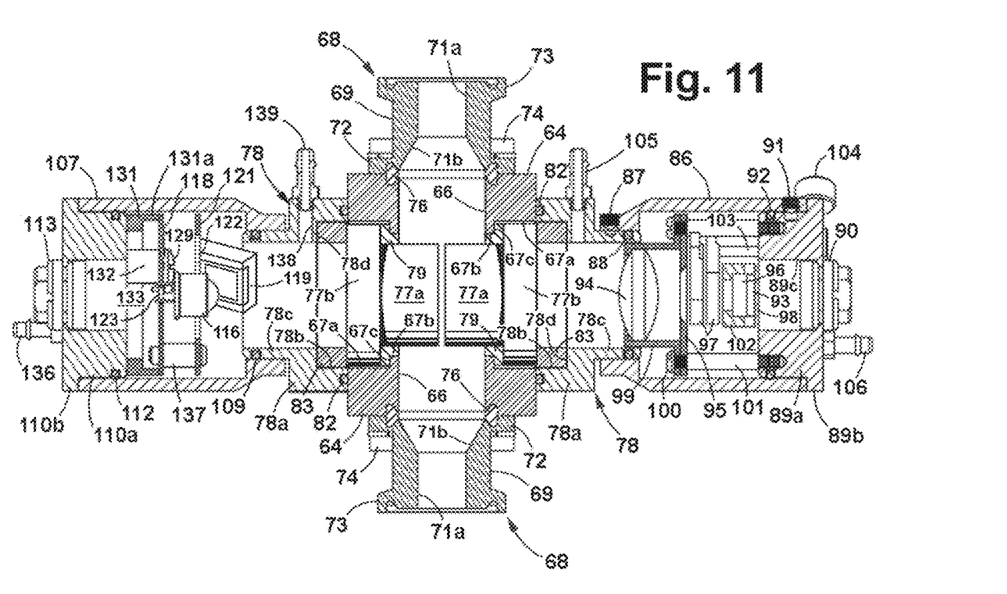
FIG. 11 is a vertical sectional view of the embodiment of FIG. 10.

The flow cell has a stainless steel body or block 64 with a flow passageway 66 opening through the upper and lower sides of the block. Monitoring ports 67 open through opposite sides of the block and intersect the passageway at right angles. The light source and detector are mounted on the block in alignment with the ports, with light from the source passing through the passageway to the detector. Both the passageway and the ports are circular in cross section.

Product lines (not shown) are connected to the flowcell block by adapters 68 having a cylindrical body 69 with an internal bore 71, a mounting flange 72 at one end of the body, and a connector 73 for the product line at the other. The adapters are secured to the block by mounting screws 74. Sealing between the block and the adapters is provided by sanitary tube fitting gaskets 76 which have generally toroidal bodies that are received in matching grooves in the confronting surfaces of the flowcell block and the mounting flanges. These gaskets have relatively short annular flanges that extend inwardly from the generally toroidal bodies, with the inner faces of the flanges aligned with the side walls of the passageway in the block and the bores in the adapters.

In the embodiment illustrated, the bore in each of the adapters has a cylindrical section 71a with the same diameter as the product line and a conically tapered section 71b which provides a smooth transition in diameter between the cylindrical section and the passageway in the flowcell body. This allows a given flowcell to be used with product lines of different diameters simply by changing adapters.

Optically transparent windows 77 are mounted in monitoring ports 67 and are retained in place by mounting rings 78. Each of the monitoring ports has an outer section 67a of relatively large diameter with a cylindrical side wall, an inner section 67b of lesser diameter that opens into flow passageway 66, and an outwardly facing annular shoulder 67c between the side walls of the two sections. The windows have solid cylindrical bodies 77a, with radial flanges 77b toward the outer ends thereof. The windows are placed in the ports with the flanges in the outer sections and the cylindrical bodies extending through the inner sections and into the passageway. Rubber gaskets 79 provide liquid-tight seals between the windows and the walls of the ports.

Window mounting rings 78 have generally rectangular bodies 78a with circular cavities 78b that correspond in diameter to the outer sections of the ports and open through the inner sides of the bodies. Cylindrical mounting flanges or sleeves 78c of lesser diameter than the cavities extend from the outer sides of the bodies, with inwardly facing annular shoulders 78d between the cylindrical side walls of the cavities and the sleeves. The mounting rings are attached to the flowcell body by mounting screws 81, with the mounting sleeves and cavities in coaxial alignment with the mounting ports and windows, and O-rings 82 providing liquid-tight seals between the mounting rings and the flowcell body.

Interchangeable spacers 83 allow the optical path length or spacing between the inner faces of the windows to be adjusted. These spacers are generally toroidal in shape and can be positioned on either or both sides of the flanges, depending upon the path length or spacing desired. In the embodiment illustrated, one relatively wide spacer is disposed on the outer side of each of the window flanges, and the path length is relatively small. The path length can be maximized by moving the spacers to the inner sides of the flanges, and intermediate path lengths can be provided by putting spacers of appropriate width on both sides of the flanges. The resiliency of rubber gaskets 79 maintains liquid-tight seals between the windows and the flowcell body notwithstanding small variations in the overall thicknesses of the spacers.

Detector 63 includes a housing having a cylindrical side wall 86 which is mounted on mounting flange 78c on the detector side of the flowcell and secured to the flange by set screws 87, with an O-ring 88 providing a liquid-tight seal between the wall and the flange. The housing also has an end piece 89 which has a solid cylindrical body 89a which fits within the side wall and a radial flange 89b which abuts against the outer end of the side wall. A hermetically sealed connector 90 is mounted in a bore 89c in the end piece for making electrical connections to the detector. The end piece is affixed to the side wall by set screws 91, and sealing between the side wall and the end piece is provided by an O-ring 92.

The optical detector includes a UV silicon detector 93 and a quartz objective lens 94 which directs UV light along the optical axis and focuses it on the detector. An aperture plate 95 and a light blocking filter 96 positioned between the lens and the detector prevent stray radiation and radiation in the visible spectrum from impinging on the detector, and a pair of calibration filters 97 are disposed between the aperture and the visible light filter.

UV detector 93 is mounted on a circuit board 98 on the inner side of end piece 89, and lens 94 is mounted in a lens holder 99 which, together with aperture plate 95, are mounted on and spaced from end piece 89 by mounting screws 100 and spacers 101. Filter 96 is mounted in a holder 102 which, together with the UV detector and circuit board 98, are attached to end piece 89 by mounting screws (not shown).

Calibration filters 97 are mounted on externally operable control shafts 103 for rotation between a normal operating position in which both filters are out of the optical path and a calibration position in which one or both of the filters are the path. The shafts can be locked in different rotational positions by thumbscrews 104 which are threadedly mounted in the outer flange of end wall 89.

An air inlet 105 mounted on window mount 78 and an air outlet 106 mounted on end piece 89 communicate with the interior of the detector housing and permit the housing to be purged with air to prevent condensation and damage to components within the housing, Light source 61 has a housing similar to the detector housing, with a cylindrical side wall 107 which is mounted on mounting flange 78c on the source side of the flowcell and secured to the flange by set screws 108, with an O-ring 109 providing a liquid-tight seal between the wall and the flange. The housing also has an end piece 110 which has a solid cylindrical body 110a that fits within the side wall and a radial flange 110b that abuts against the outer end of the side wall. The end piece is affixed to the side wall by set screws 111, and an O-ring 112 provides liquid-tight sealing between the side wall and the end piece. A hermetically sealed electrical connector 113 is mounted on the end piece for connection to external circuits which carry electrical signals and power for the device.

Figures 13, 14, 15:
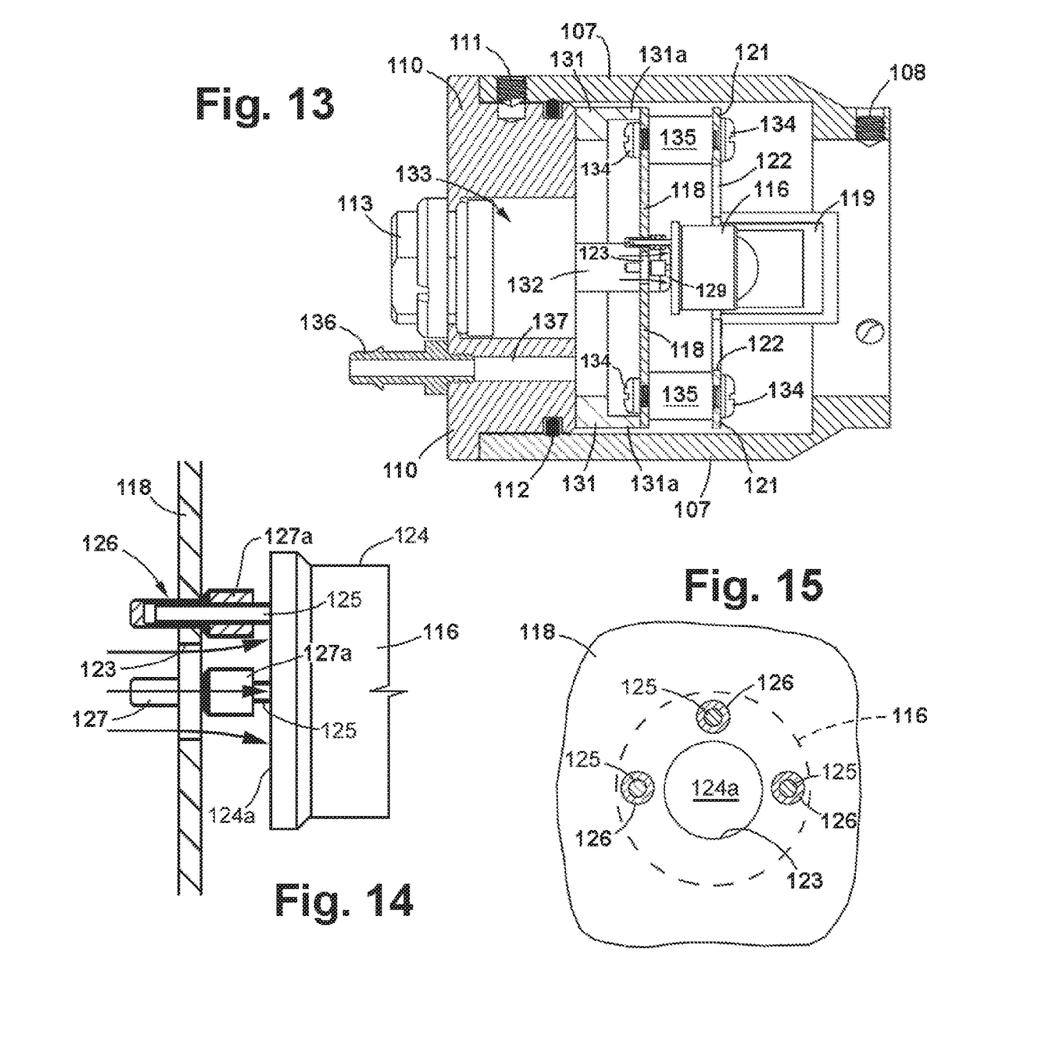
FIG. 13 is an enlarged, vertical sectional view of the UV light source in the embodiment of FIG. 10, with the source rotated 22.5 degrees from the position in which it is shown in FIG. 11.
FIG. 14 is an enlarged view of a portion of the structure shown in FIG. 13.
FIG. 15 is an end elevational view of the structure shown in FIG. 14.
Figure 16:
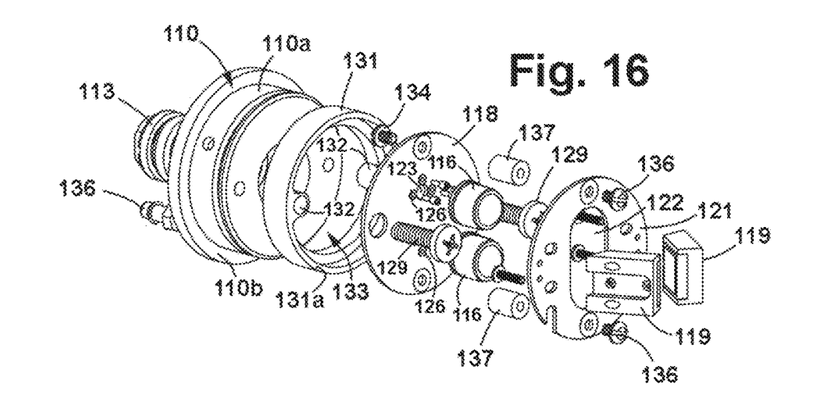
FIG. 16 is an exploded, isometric view similar to FIG. 12 of another embodiment of a UV light source incorporating the invention.
Figure 17:
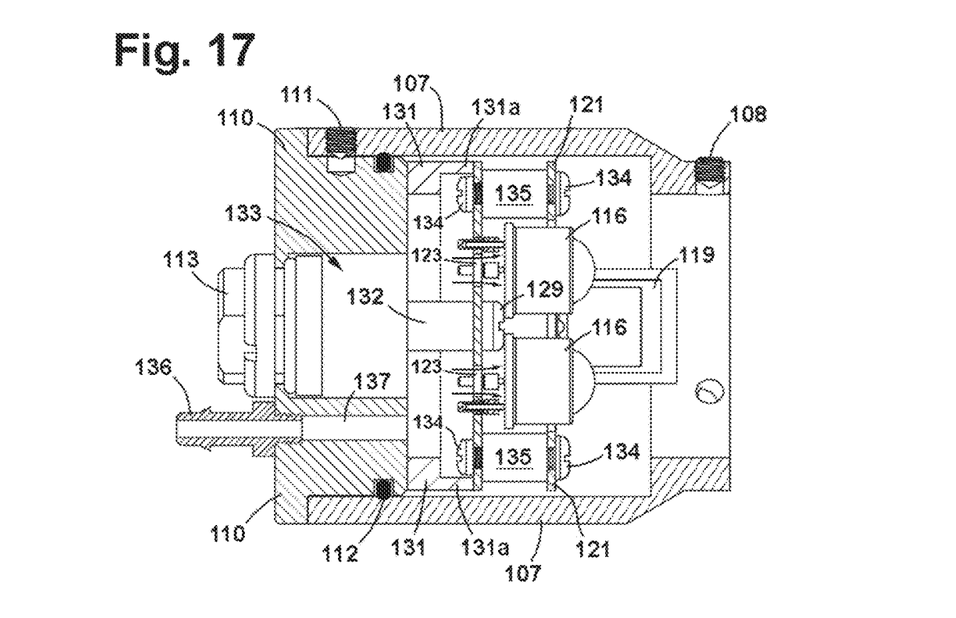
FIG. 17 is a vertical sectional view similar to FIG. 13 of the embodiment of FIG. 16.
Figure 18:
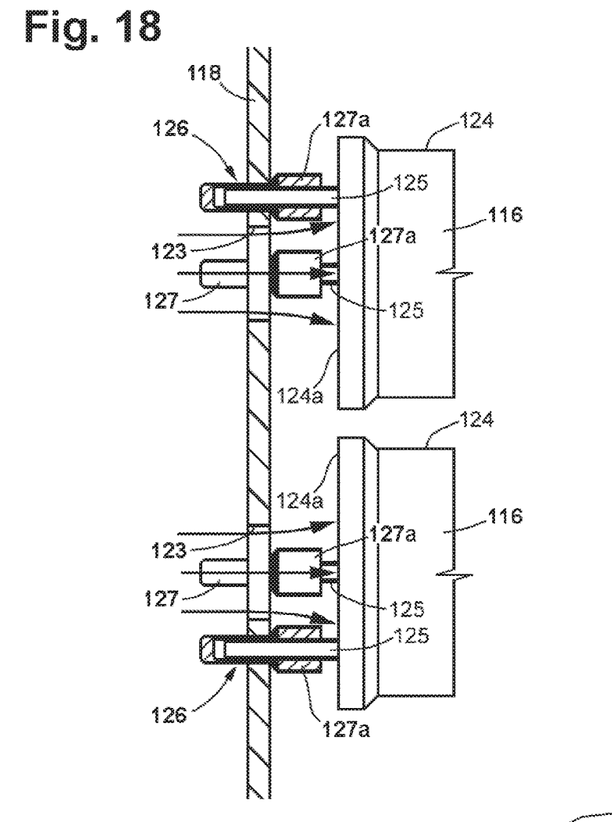
FIG. 18 is an enlarged view of a portion of the structure shown in FIG. 17.
Figure 19:
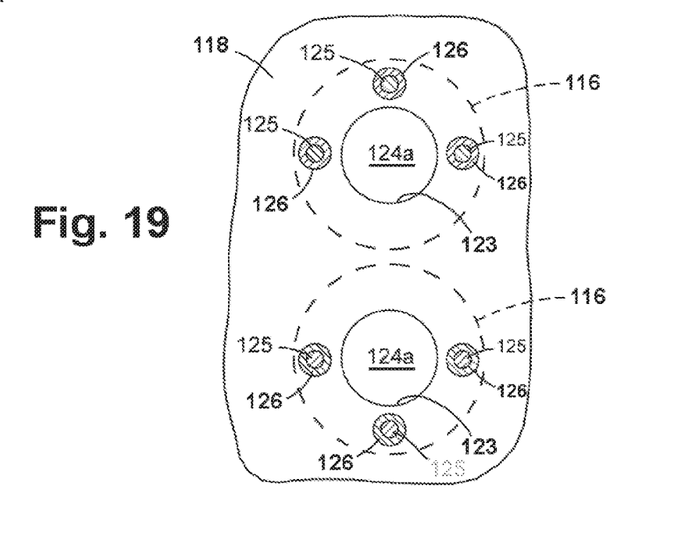
FIG. 19 is an end elevational view of the structure shown in FIG. 18.

Light source 61 is similar to the light source in the embodiment of FIGS. 4-5 in that it includes a solid state UV emitter or LED (light emitting diode) 116 mounted on a circuit board 118 and a pair of reference detectors 119 mounted on a second circuit board 121 which is spaced from the first board and has an opening 122 through which the emitter extends.

However, light source 61 differs from the earlier embodiment in that it includes means for cooling the LED. The cooling of LED diodes is particularly important when using LEDs in the near and far UV spectra. As the temperature of the LED increases, the expected output of the LED is reduced proportionally to the increase in temperature, and the anticipated life of the LED may be reduced by as much as one half for every 10° C. rise in temperature above ambient (25° C.).

A typical UV diode has a voltage drop of 5-6 VDC and is driven by a constant current power source at 25 mA, resulting in a dissipation of approximately 150 mW, which can generate temperatures that adversely affect the diode output and life. To avoid such losses and obtain optimum output and life, LEDs have been mounted on heatsinks or cooled by the use of Peltier cooling devices. However, there are many applications in which the use of heatsinks is difficult and the use of a Peltier device is not practical, particularly where the removal of heat from the Peltier device also requires a heatsink and/or a cooling fan.

In the embodiment of FIGS. 10-15, the means for cooling the LED includes a ventilation opening 123 in the circuit board directly beneath the LED, with the LED being spaced away from circuit board so that air can pass through the opening and around the LED. The type of LED employed in the invention is typically packaged in a TO-18 or TO-39 package, and the semiconductor die is attached to the base 124a of case 124, with the case serving as a first heatsink for the device. With the vent opening directly beneath the LED, the air flowing through the opening is directed to the base of the case at the optimal location to cool the die attached to it.

As used herein, the term "beneath the LED" refers to the relative positioning of the LED and the vent opening without regard to the orientation of the two. It means that the opening is positioned directly opposite the base of the LED housing or case, not that the opening is physically below or lower than the LED. Thus, in the embodiments illustrated, even though the LED is turned on its side and the opening is positioned to one side of the LED, the opening is still beneath the base of the LED.

Figure 12:
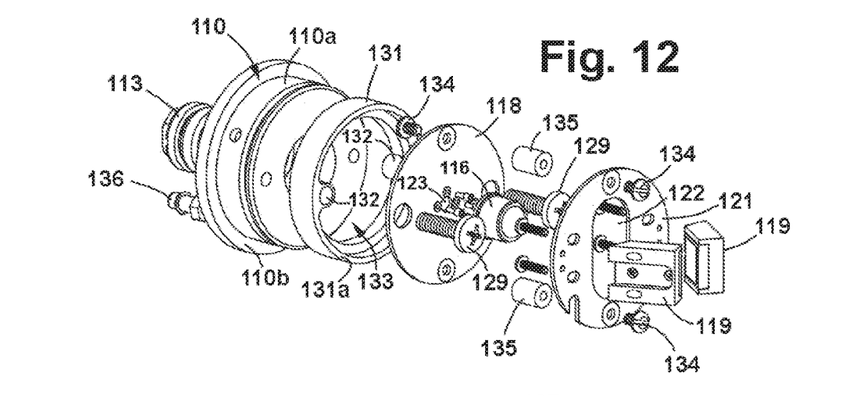
FIG. 12 is an exploded, isometric view of the UV light source in the embodiment of FIG. 10, with the source rotated 22.5 degrees from the position in which it is shown in FIG. 11.

As best seen in FIGS. 12-14, the leads or pins 125 of the LED are received in individual pin sockets 126 which are soldered directly to the circuit board and spaced about the opening in the board. The sockets include adapters 127 with enlarged end portions 127a which receive the leads and help to space the LED away from the board. The leads are trimmed such that when they are fully inserted into the sockets, the base does not come in contact with the sockets, thereby limiting the thermal conductivity path to just the leads themselves.

Circuit board 118 is attached to end piece 110 by mounting screws 129, with a spacer 131 between the two. This spacer has a cylindrical outer wall 131a with a pair of diametrically opposed bosses 132 through which the mounting screws pass. The annular ends of the outer wall are in sealing engagement with the inner face of the end piece and the under side of the circuit board, with the end piece, outer wall, and circuit board forming a chamber 133 which is air tight except for the opening beneath the LED. The second circuit board 121 is attached to the first by mounting screws 134 and spacers 135 outside the chamber. Vent opening 123 is a relatively small, circular opening, whereas opening 122 is a relatively tall oval-shaped opening in which the LED is centered.

Air is introduced into chamber 133 through an inlet fitting 136 and an inlet passageway 137 which extends through end piece 110 and opens into the chamber. After passing through the opening 123 in circuit board 118 and around the LED, the air exits the housing through a passageway 138 in window mount 78 on the source side of the flowcell, with an outlet fitting 139 at the outer end of the passageway.

The air requirement is small, typically on the order of only 10-20 liters per hour (LPH), and with the short air path, the air reaching the LED will be substantially at the incoming air temperature. With the cooling provided in this embodiment, the output and the life of the LED are greatly improved and should meet the manufacturer's specifications under all but the most extreme conditions.

The light source shown in FIGS. 16-19 is similar to the embodiment of FIGS. 11-15 except it has a second solid state UV emitter or LED 116. The two LEDs are mounted side-by-side on circuit board 118 on opposite sides of the optical axis. Both LED's extend through the oval-shaped opening 122 in circuit board 121, and the beams from both of the LEDs are directed along the axis toward the flowcell and the measurement detector.

A vent opening 123 is formed in circuit board 118 directly beneath the base 124a of each of the LEDs, and both LEDs are spaced away from the board so that air from plenum chamber 133 can flow through the openings and around the LEDs to cool the LEDs in the manner discussed above.

Figure 20:
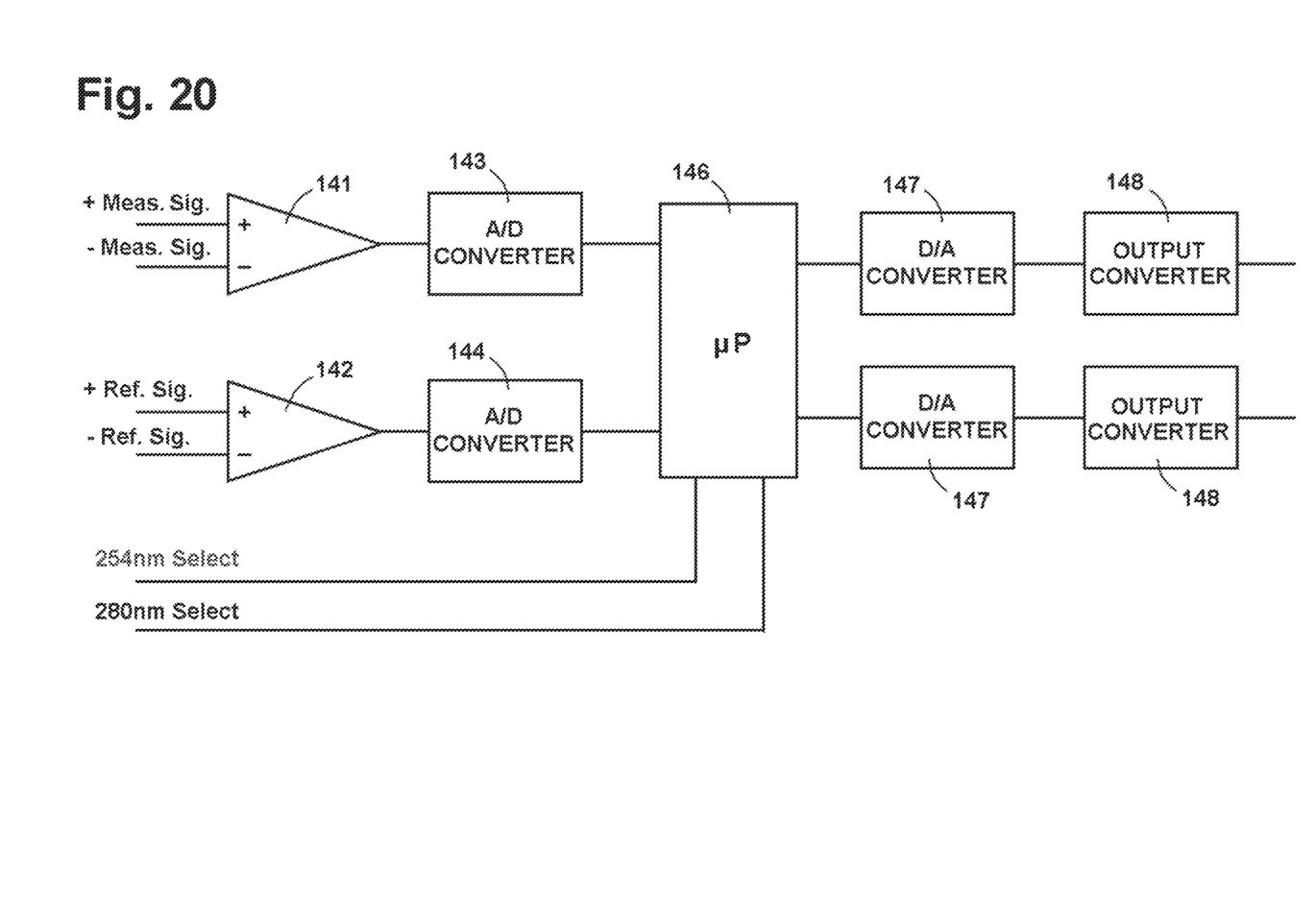
FIG. 20 is a simplified block diagram of circuitry for processing signals from systems with single LED and dual LED light sources according to the invention.

As illustrated in FIG. 20, the measured input process signal from sensor detector 93 and the reference signals from the detectors 119 that monitor the output of UV LED emitter 116 are amplified by amplifiers 141, 142 and applied to 16-bit analog-to digital converters 143, 144 which are controlled by a microprocessor 146. The A/D converters can be of moderate speed, for example, with sample rates of 10,000 samples per second. These samples are converted to the logarithms of the measured signals following which the log ratio of these signals is computed by the microprocessor to compensates for intensity changes in the UV LED output.

The log ratio signals are applied to two output channels, each of which includes a digital-to-analog converter 147 and a current loop output converter 148. The signals can be applied in different ways. For example, the output for one channel can be the full range of the measurement, and the output for the other can be an offset or expanded value of the log ratio.

When the sensor utilizes dual UV LEDs, the microprocessor can select the LED and synchronize its measurement and reference signals is the manner described above. The response of the LED emitters is such that switching rate of 1-3 kHz is quite reasonable. With two LEDs operating at wavelengths of 254 nm and 280 nm, for example, the output of one channel would be the log ratio of one selected LED 1 (i.e., 254 nm) and then the output of the other channel would be the log ratio of the other selected LED (i.e., 280 nm).

The invention has a number of important features and advantages. With the solid state UV emitters, the source itself provides UV emissions at the wavelength and bandwidth desired, and the need for filtering to isolate the emissions of interest is eliminated. The emissions are noise free and stable, and being concentrated at a single wavelength, the output exceeds that of a gas discharge lamp at the desired wavelength.

The power consumed by a solid state UV emitter is typically on the order of 50-100 milliwatts, which is substantially less than the 4-5 watts required by a typical discharge lamp. Thus, in addition to being more efficient and eliminating the need for costly power supplies, the solid state emitter is an intrinsically safe device that can be operated in most hazardous environments without explosion-proof housing and/or special cabling. Solid state UV emitters also have fast turn-on characteristics and attain a stable output in microseconds, which permits operation at multiple wavelengths simply by turning emitters of different wavelengths on and off in sequence. Moreover, the small size of the devices permits multiple devices to be mounted on a single circuit board for multiple wavelength operation with no alteration or modification of the optical system.

Although the spectral output of the UV solid state emitter is stable with respect to time, the output is inversely proportional to temperature, and the reference detectors provide compensation for temperature related drift.

In the embodiments in which the LEDs are cooled, having the vent openings directly beneath the bases of the LEDs minimizes the air path and directs the air toward the central area of the base where the active wafer of the LED is located and the cooling is most effective.

Thermal conduction between the LED and the circuit board is minimized, and with the cooling, the output and the life of the LED are greatly improved and should meet the manufacturer's specifications under all but the most extreme conditions.

While the invention has been disclosed primarily in connection with new installations, it can also be incorporated into existing systems simply by replacing the gas discharge lamp and power supply with a solid state UV emitter and simple regulator circuit. When used in such systems, the inclusion of UV solid state emitter source will be substantially transparent and require little or no modifications or special calibration.

It is apparent from the foregoing that a new and improved UV light source has been provided. While only certain presently preferred embodiments have been described in detail, as will be apparent to those familiar with the art, certain changes and modifications can be made without departing from the scope of the invention as defined by the following claims.

The invention claimed is:

1. An air cooled light source for an inline optical sensor, comprising a housing in which a plenum chamber is formed, a circuit board forming one wall of the plenum chamber, a solid state UV emitter mounted on and spaced from the circuit board outside the plenum chamber, a ventilation opening in the circuit board directly beneath the solid state UV emitter, an air inlet through which air for cooling the solid state UV emitter is supplied to the plenum chamber, and an air outlet through which air can leave the housing after flowing from the plenum chamber through the ventilation opening and around the solid state UV emitter.

2. The air cooled light source of claim 1 wherein the solid state UV emitter is mounted in a case having a thermally conductive base with a semiconductor die mounted on the base, and the ventilation opening is positioned such that air passing through the opening impinges directly on the base to cool the die.

3. The air cooled light source of claim 1 including a second circuit board spaced from the first named circuit board outside the plenum chamber, with an opening in the second circuit board through which the solid state UV emitter extends and air flowing around the solid state UV emitter can pass to the outlet.

4. The air cooled light source of claim 1 wherein electrical leads of the solid state UV emitter are received in individual pin sockets mounted on the circuit board and spaced about the ventilation opening.

5. The air cooled light source of claim 1 wherein the solid state UV emitter emits a single band of light with wavelengths in the range of 240 to 400 nm and a bandwidth on the order of 10-20 nm.

6. The air cooled light source of claim 1 including a second solid state UV emitter mounted on and spaced from the circuit board and a second ventilation opening in the circuit board directly beneath the second solid state UV emitter through which air can flow to cool the second solid state UV emitter.

7. The air cooled light source of claim 6 including a second circuit board spaced from the first named circuit board outside the plenum chamber, with an opening in the second circuit board through which the two solid state UV emitters extend and air flowing around the two solid state UV emitters can pass to the outlet.

8. The air cooled light source of claim 6 wherein the solid state UV emitters emit light at wavelengths of 254 nm and 280 nm, with bandwidth on the order of 10-20 nm, respectively.

9. An air cooled light source for an inline optical sensor, comprising a housing, a plenum chamber within the housing, an inlet through which air can enter the plenum chamber, a solid state UV emitter which has a thermally conductive case and is mounted on a circuit board which forms one wall of the plenum chamber, a ventilation opening in the circuit board directly beneath the emitter for directing air from the plenum chamber into direct contact with the thermally conductive case of the emitter, with electrical leads of the emitter being received in individual pin sockets mounted on the circuit board and spaced about the ventilation opening, and an air outlet through which air can leave the housing after cooling the solid state UV emitter.

10. The air cooled light source of claim 9 wherein the plenum chamber is air-tight except for the air inlet and the ventilation opening.

11. An air cooled light source, comprising a housing, a circuit board spaced inwardly from an end wall of the housing, a spacer having a peripheral side wall extending between the end wall and the circuit board to form a closed chamber bounded by the end wall, the side wall, and the circuit board, a solid state UV emitter mounted on and spaced from the circuit board outside the chamber, an air inlet communicating with the chamber for supplying air to the chamber for cooling the emitter, and an opening in the circuit board directly beneath the emitter through which air from the chamber can pass to the emitter.

12. The air cooled light source of claim 11 wherein the circuit board and the spacer are attached to the end wall by mounting screws which pass through the circuit board and the spacer and are threadedly received in the end wall.

13. The air cooled light source of claim 11 wherein electrical leads of the solid state UV emitter are received in individual pin sockets mounted on the circuit board and spaced about the opening.

14. The air cooled light source of claim 11 wherein the plenum chamber is air-tight except for the air inlet and the opening in the circuit board.

15. The air cooled light source of claim 11 including a second circuit board spaced from the first named circuit board, with an opening in the second circuit board through which the solid state UV emitter extends and air flowing around the emitter can pass.

16. The air cooled light source of claim 11 including a second solid state UV emitter mounted on and spaced from the circuit board and a second opening in the circuit board directly beneath the second solid state UV emitter through which air can flow to cool the second solid state UV emitter.

* * * * *